US008137905B2

(12) United States Patent
Brauner et al.

(10) Patent No.: US 8,137,905 B2
(45) Date of Patent: Mar. 20, 2012

(54) APPARATUS AND METHOD FOR DETERMINING AN ANALYTE IN A FLUID (75) Inventors: Michael Brauner, Burstadt (DE); Thomas Kotnig, Graz (DE); Dieter Mangold, Maxdorf (DE); Norbert Oranth, Hirschberg (DE); Christoph Ritter, Graz (AT); Gerd Schweiger, Graz (AT); Valerie Winckler-Desprez, Ladenburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 710 days.

(21) Appl. No.: 11/969,278

(22) Filed: Jan. 4, 2008

(65) Prior Publication Data

US 2008/0220539 A1    Sep. 11, 2008

(30) Foreign Application Priority Data

Jan. 10, 2007   (EP) .................................. 07000433

(51) Int. Cl.
  *C12Q 1/00* (2006.01)
(52) U.S. Cl. .......................................................... 435/4
(58) Field of Classification Search .................. None
  See application file for complete search history.

(56) References Cited

U.S. PATENT DOCUMENTS

| | | | | |
|---|---|---|---|---|
| 4,867,797 A * | 9/1989 | Thomasen et al. | ............... | 134/18 |
| 5,028,142 A | 7/1991 | Ostoich et al. | | |
| 5,110,727 A * | 5/1992 | Oberhardt | ..................... | 435/13 |
| 5,222,808 A | 6/1993 | Sugarman et al. | | |
| 5,795,784 A * | 8/1998 | Arnquist et al. | ................. | 436/50 |
| 6,007,690 A * | 12/1999 | Nelson et al. | .................. | 204/601 |
| 6,066,448 A * | 5/2000 | Wohlstadter et al. | ......... | 435/6.11 |
| 7,598,371 B2 * | 10/2009 | Willson et al. | ................ | 536/25.4 |
| 2002/0187501 A1 * | 12/2002 | Huang et al. | ..................... | 435/6 |
| 2004/0038355 A1 | 2/2004 | Vogt et al. | | |
| 2004/0228212 A1 | 11/2004 | de Goor et al. | | |
| 2004/0235196 A1 | 11/2004 | Colin | | |

FOREIGN PATENT DOCUMENTS

| | | |
|---|---|---|
| EP | 0545284 A1 | 6/1993 |
| JP | 2006266836 | 4/2008 |
| WO | WO 9843739 A2 | 10/1998 |
| WO | WO02054417 A1 | 7/2002 |
| WO | WO 03011443 A2 | 2/2003 |
| WO | WO 03031977 A2 | 4/2003 |

OTHER PUBLICATIONS

Ryu, K., Shaikh, K., Goluch, E., Fan, Z., Liu, C. "Micro magnetic stir-bar mixer integrated with parylene microfluidic channels", Lab Chip, 2004, 4, 608-613.
Hurtley, S., "Editor's Choice Column", Science 293, (2001), pp. 1731-1733.
Stroock et al., "Chaotic Mixture for Microchannels", Science 295, 647-651 (2002).

* cited by examiner

*Primary Examiner* — Ann Lam
(74) *Attorney, Agent, or Firm* — McDonnell Boehnen Hulbert & Berghoff LLP (57) ABSTRACT The invention relates to an apparatus and a method for determining an analyte in a fluid. Provided in the device is a stirring zone formed in an optionally microfluidic three-dimensional structure, into which stirring zone a sample of the fluid can be introduced and in which there is a stirring device which can be operated in a contactless manner and is optionally designed as a microstirrer, the stirring device being configured so as to stir the sample of fluid introduced into the stirring zone and being loaded with at least one reagent which reacts with the analyte. The invention also provides a stirring device which can be operated in a contactless manner and is optionally designed as a microstirrer, the stirring device being loaded with the at least one reagent which reacts with the analyte.

30 Claims, 4 Drawing Sheets

APPARATUS AND METHOD FOR DETERMINING AN ANALYTE IN A FLUID

BACKGROUND OF THE INVENTION

The invention relates to an apparatus for determining an analyte in a fluid, and to a method.

Figure 1:
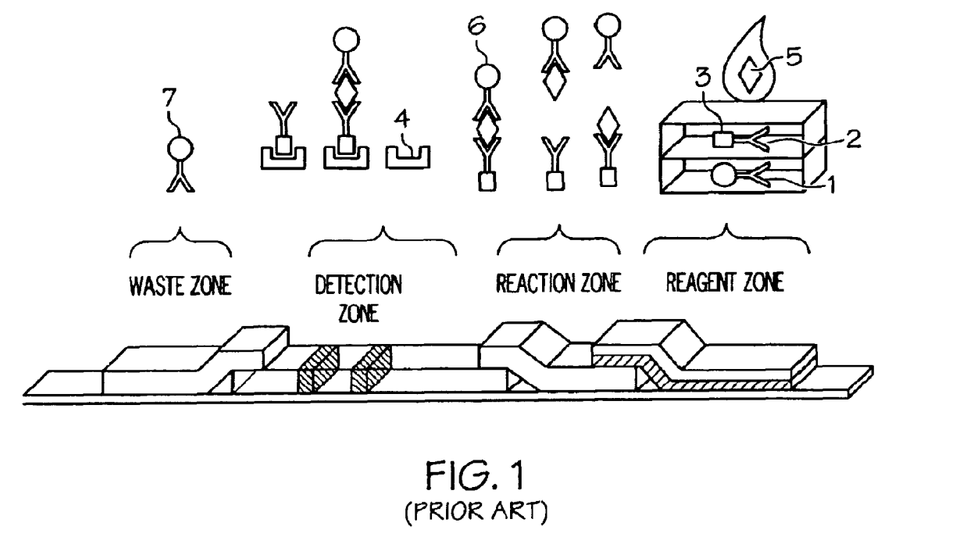
FIG. 1 shows a schematic view of a test strip for determining an analyte in a fluid according to the prior art.

Such an apparatus for determining an analyte in a fluid is known for example in the form of test strips or test systems, as sold inter alia under the trade name "Roche Cardiac Reader". FIG. 1 shows a known test strip which comprises a plurality of bonded nonwovens and on which a reagent zone and a detection zone are formed. Located in the reagent zone are one or more reagents 1, 2 which react with the analyte 5 to be determined, for example an antigen such as troponin which is present in the fluid. In order to determine the analyte 5, a sample of the fluid is applied to a detachable nonwoven in the reagent one, whereupon the fluid, for example a blood sample, penetrates into the nonwoven material. In the case of blood samples, cellular components are left behind. In the reaction zone formed on the test strip, the analyte 5 to be determined and the one or more reagents 1, 2 react to form at least one reaction product 6. In the illustrated embodiment according to the prior art, a first reagent 1 is a conjugate composed of a first antibody and gold particles. A second reagent 2 is an antibody labelled with biotin 3. The detection zone contains a streptavidin 4 bound to a nonwoven material.

As the analyte 5 to be determined reacts with the first and second reagent 1, 2, the reaction product 6 is produced, which is a sandwich-type compound. By means of capillary forces, the fluid is transported along the test strip through the different nonwoven sections, wherein the reaction product 6 is bound to the streptavidin 4 in the detection zone by means of the biotin residue 3. Unbound residues 7 are further transported past the detection zone in the test strip to a waste zone. The analyte 5 in the detection zone can then be detected, for example by a quantitative detection based on remission measurements of the absorption values in the detection zone. Other methods for detecting the reaction product are based on electrochemical, other optical or physical methods.

A further embodiment of a known test strip is described for example in the document EP 1 061 369 A2.

However, the known test strips based on nonwoven materials have the disadvantage that a large quantity of the applied sample of fluid is lost within the nonwoven material. It is therefore necessary, for the analysis that is to be carried out, to apply a much greater quantity of sample than would be necessary for the actual determination of the analyte. In order to avoid this disadvantage, there have been proposed apparatuses comprising a three-dimensional structure in which the reagent zone, the reaction zone, the detection zone and optionally the waste zone are arranged one behind the other as regions or sections of the three-dimensional structure and are in fluid connection with one another via a channel structure. Test elements or systems with channel-like structures are thus obtained. In a manner similar to the test strips, in one embodiment, during the determination, a first and a second reagent are mixed with the sample of fluid in the channel-like structure, whereupon the analyte in the fluid reacts with the two reagents to form a reaction product.

As a further zone, a trapping zone may be provided in the three-dimensional structure. This trapping zone is a section of the three-dimensional structure in which for example the second reagent is immobilised, so that a complex composed of the analyte to be determined and the first reagent binds thereto, the complex being formed in a reaction beforehand and thus being a reaction product. The second reagent formed as an antibody can be immobilised directly on a surface in the region of the trapping zone of the three-dimensional structure. Alternatively, an antibody labelled for example with biotin or in an equivalent manner can also be immobilised on the section of the trapping zone which is coated with a suitable receptor. The section of the three-dimensional structure formed as the trapping zone may be a flat surface or a three-dimensional spatial structure. Examples of a three-dimensional trapping zone include porous layers, for example made from a nonwoven, or hydrophilic polymers, for example gels.

The three-dimensional structure for forming the combination of different zones for the test systems may be formed for example in microtitre plates. The three-dimensional structure may preferably be designed as a microfluidic structure. Such structures can be formed from various materials using different production methods, for example by means of laser structure machining or injection moulding techniques. One feature common to the various embodiments is the fact that the sample of fluid containing the analyte to be determined has to be brought into contact with one or more reagents which react with the analyte. For this purpose, it is provided for example in the document WO 98/43739 that one or more reagents are arranged in the region of a surface section of a capillary region of a three-dimensional structure, through which the sample of fluid flows. In this way, in the known test apparatus, a target ligand or a conjugate is immobilised on the surface sections.

On the other hand, in three-dimensional structures into which one or more fluids are introduced, it is known to provide mixing zones for mixing different fluids with one another or for mixing one or more fluids with dry substances. The conditions and thus the mixing processes differ specifically depending on the dimensions of the three-dimensional structure. There are exceptions in the case of microstructures or microfluidic structures, since conditions associated with a low Reynolds number prevail (cf. K Suk et al.: "*Micro magnetic stir-bar mixer integrated with parylene microfluidic channels*", Lab Chip 2004, 4, pages 608-613). It has been proposed to use magnetic stirrers to stir fluids in microfluidic structures. In this case, a stirring element is arranged in the microfluidic structure and is driven by means of an external magnetic field. A mixing device based on a similar principle is disclosed in the document U.S. Pat. No. 5,028,142, which can be used inter alia for immunological agglutination assays.

The document U.S. Pat. No. 5,222,808 proposes an apparatus which can be used to analyse liquid biological samples. In said document, the fluid transport in the apparatus is based on capillary farces. In a mixing chamber of the apparatus, reagents which are present in the mixing chamber can be mixed with the sample with the aid of magnetic particles. The analysis of the sample can take place in the mixing chamber itself or in a downstream detection zone by means of optical methods.

SUMMARY OF THE INVENTION

It is against the above background that the present invention provides certain unobvious advantages and advancements over the prior art. In particular, the inventors have recognized a need for improvements in apparatus and methods for determining an analyte in a fluid.

Although the invention is not limited to specific advantages or functionality, it is noted that the present invention provides for determination of the analyte with the smallest possible sample volume and also with a high degree of accuracy and sensitivity.

In accordance with one embodiment of the present invention, there is provided an apparatus for determining an analyte in a fluid comprising a stirring zone formed in a three-dimensional structure, into which stirring zone a sample of the fluid can be introduced and in which there is a stirring device which can be operated in a contactless manner, said stirring device being configured so as to stir the sample of fluid introduced into the stirring zone and being loaded with at least one reagent which resets with the analyte, wherein the stirring device is a magnetic stirring device comprising one or more magnetic strip sections which form stirring elements. The stirring zone can optionally be formed in a microfluidic three-dimensional structure and the stirring device can optionally be designed as a microstirrer.

In accordance with another embodiment of the present invention, there is provided a method for determining an analyte in a fluid comprising introducing a sample of the fluid into a three-dimensional structure with a stirring zone, stirring the introduced sample of fluid by a stirring device which is arranged in the stirring zone and can be operated in a contactless manner, the stirring device being loaded with at least one reagent which reacts with the analyte, reacting the at least one reagent with the analyte in the sample of fluid so as to form a reaction product, and determining the analyte by detecting the at least one reaction product or optionally a further reaction product formed by the reaction product. The stirring device can optionally be designed as a microstirrer.

In accordance with yet another embodiment of the present invention, also provided is a stirring device which can be operated in a contactless manner, the stirring device being loaded with at least one reagent which reacts with an analyte, wherein the stirring device is designed as a magnetic stirring device comprising one or more magnetic strip sections which form stirring elements.

These and other features and advantages of the present invention will be more fully understood from the following detailed description of the invention taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

By virtue of the invention, the reaction between the analyte and the at least one reagent which reacts with the analyte, which reaction is necessary to determine the analyte, can be carried out with great efficiency by optimising the contact between the at least one reagent and the analyte by means of stirring in the stirring zone. During the stirring operation, the fluid continuously flows round the stirring device which is loaded with the at least one analyte. This is such that a local exchange of particles continuously takes place in sub-volumes of the stirring zone, so that the probability of a meeting between as-yet-unreacted particles of the at least one reagent on the one hand and the sample of fluid on the other hand is increased. Here, the sample of fluid and the at least one reagent may be mixed directly with one another or else may be brought into contact only in an interface region. In one possible embodiment, the latter is the case for example when the at least one reagent is permanently immobilised on the stirring device. Overall, the available volume of the sample of fluid is thus efficiently used for detection of the analyte, and this makes it possible to keep the required volume of sample as low as possible.

The apparatus according to the invention and the method according to the invention are suitable for example for determining analytes in biological samples, particularly in blood and sample materials derived therefrom, such as serum and plasma, urine, saliva, sweat or the like. The analytes may in this case be tested for example by means of enzymatic principles or principles based on specific binding reactions. These are typically immunological test principles or test principles based on the binding of complementary nucleic acids. Suitable analytes are in particular metabolites, for example glucose, lactate, cholesterol, creatinine and the like, or immunologically active substances such as antigens, antibodies or haptens. Preference is given to the detection of immunologically detectable marker substances, for example troponin T, troponin I, BNP, NTproBNP, myoglobin, D-dimer, CK-MB or the like. The detection principles and the associated reagents, particularly biochemical reagents such as enzymes, antibodies, antigens or labelled substances, are known per se to the person skilled in the art.

One further development of the invention provides that the stirring device has pore structures with pores in which the at least one reagent which reacts with the analyte is at least partially embedded. Pore structures may be provided for example by using nonwoven materials or woven materials for the stirring device. Membrane materials have proven to be particularly suitable, especially nitrocellulose membranes such as the reinforced nitrocellulose membrane Purabind A-RP (pore size 8 µm) from the company Whatman.

One embodiment of the invention provides that the magnetic stirring device comprises magnetic particles which, when an external field is applied, accumulate to form stirring elements formed by groups of magnetic particles. As a result, the stirring elements are formed for example by rod-shaped structures, unlike in other embodiments such as sheet-like stirring elements for example.

One further development of the invention provides that the magnetic strip sections can be formed for example using magnetic tapes such as those known for audio tapes or video tapes. Magnetic layers located on plastic films of small plates are generally suitable, and these will also be referred to below as "film with magnetic layer". By way of example, a polyester tape with a magnetic layer (audio tape) having an overall thickness of 0.045 mm (CMC Klebetechnik GmbH) has proven to be suitable, and this may also be a self-adhesive polyester tape if necessary.

In another embodiment of the present invention, it may be provided that the stirring device has at least one stirring sub-element selected from the following group of stirring sub-elements: a laminated section, a woven section, a nonwoven section, a membrane section, and a film section. Suitable materials for these sections are, for example, glass fibre non-wovens, double-sided adhesive tapes or polyester tapes with a magnetic layer or self-adhesive polyester tapes with a magnetic layer and also reinforced nitrocellulose membranes.

One further development of the invention may provide that the at least one reagent which reacts with the analyte is bound to the stirring device by at least one binding type selected from the following group of binding types: partially detachable from the stirring device during stirring of the sample of fluid, substantially completely detachable from the stirring device during stirring of the sample of fluid, and substantially non-detachable from the stirring device during stirring of the sample of fluid. If the at least one reagent which reacts with the analyte is used in such a way that the at least one reagent is substantially non-detachable from the stirring device during stirring of the sample of fluid, in this way a trapping zone is formed on the stirring device, in the area of which the analyte to be detected accumulates. Such a bound reagent is for example streptavidin. For example, part of the surface of the stirring device can be coated with streptavidin in such a way that a biotin-labelled antibody of another reagent or the biotin-labelled sandwich-type compound, as described above, binds to the streptavidin applied to the surface. The bound reagent may also be an antibody. By way of example, the analyte may be troponin I or troponin T, and the corresponding antibody or antibodies are polyclonal or monoclonal antibodies against troponin I or troponin T. In the same way, other analytes such as other cardiac or neurohormonal markers can be detected with corresponding antibodies or antibody pairs. The antibodies may be immobilised on the stirring device in a manner known per se.

One further development of the invention provides that the stirring device has, at least in sub-regions, a coating which optionally promotes the adhesion of the at least one reagent which reacts with the analyte.

In one convenient embodiment of the invention, it may be provided that the at least one reagent which reacts with the analyte is formed as at least one dry reagent on the stirring device.

One advantageous embodiment of the invention provides that the at least one reagent which reacts with the analyte is formed in a layer arrangement on the stirring device, which layer arrangement at least partially covers one surface of the stirring device.

One further development of the invention provides that the layer arrangement comprises superposed layers of different reagents which react with the analyte.

In one advantageous embodiment of the invention, it may be provided that the different reagents in layers of the layer arrangement which react with the analyte have different solubilities during stirring of the sample of fluid with the stirring device. As a result it is possible to incorporate a plurality of reagents into the reaction one after the other during the stirring of the sample of fluid, according to a desired progress of the reaction. For instance, it may be provided that one or more layers of reagents detach from the stirring device, whereas a lowermost layer of the layer arrangement remains substantially completely on the stirring device, i.e., cannot be detached by the fluid, and thus can act for example as a trapping reagent for a trapping zone. By way of example, an antibody directed against an analyte may be present on the stirring device in a permanently immobilised manner, optionally immobilised via a biotin/streptavidin interaction, while an antibody labelled with an optically or visually detectable label is present on the stirring device in a detachable manner. Particularly in the case of flat stirring devices, the detachable reagent may be present on one side of the stirring device, while the immobilised reagent is applied to the opposite side of the flat stirring device.

Furthermore, it may be provided that only some of the reagents required for detecting the analyte are immobilised on the stirring device, while other reagents are supplied to the sample in some other way, for example by adding the reagent to the sample or placing it in dissolvable form in the three-dimensional structure into which the sample is introduced.

One further development of the invention may provide that a reaction zone is also formed in the three-dimensional structure. In the area of the reaction zone, usually at least one reaction between the at least one reagent and the analyte to be determined takes place.

One further development of the invention provides that a detection zone is also formed in the three-dimensional structure. In the detection zone, a product of the reaction between the at least one reagent and the analyte to be determined, or a further reaction product derived therefrom, can be detected in order to detect the analyte, by means of one of the following methods: optical detection methods, electrochemical detection methods and physical detection methods. Optical detection methods are based on measuring the absorption, transmission, reflection, remission, scattering, luminescence or the like. The remission or luminescence is measured, in particular the fluorescence. Electrochemical detection methods are based on amperometry, potentiometry or conductometry.

In one convenient embodiment of the invention, it may be provided that a waste zone is also formed in the three-dimensional structure.

One advantageous embodiment of the invention provides that a trapping zone is also formed in the three-dimensional structure, a trapping reagent being immobilised in the trapping zone. The trapping reagent is immobilised, on the wall of the three-dimensional structure and/or the stirring device, optionally initially covered by reagent(s) which react(s) with the analyte.

One further development of the invention provides that one or more zones selected from the following group of zones are arranged, downstream of the stirring zone in the three-dimensional structure and are connected to the stirring zone via an optionally microfluidic channel structure: a reaction, zone, a detection zone, a trapping zone and a waste zone.

In one advantageous embodiment of the invention, it may be provided that the channel structure is formed so as to transport the sample of fluid using capillary forces.

One further development of the invention may provide that one or more zones selected from the following group of zones are formed in the three-dimensional structure and are integrated with the stirring zone: the reaction zone, the detection zone, the trapping zone and the waste zone.

One further development of the invention provides that a wall of the three-dimensional structure is loaded at least in wall sub-regions with at least one further reagent which reacts with the analyte.

In one convenient embodiment of the invention, it may be provided that the at least one reagent which reacts with the analyte and optionally the at least one further reagent which reacts with the analyte contain one or more reagent constituents selected from the following group of reagent constituents: luminescent dye, phosphorescent, dye, absorption dye, coloured particles, labelled antibodies, and antibodies with a binding group for binding the antibodies to an associated receptor. A large number of reagent constituents are known per se. Reference is made to the following reagents purely by way of example: (poly)streptavidin in conjunction with biotinylated antigens or antibodies, antigens and antibodies labelled with metal particles, in particular gold, selenium or carbon, antigens or antibodies labelled with enzymes or fluorescent dyes, antigens or antibodies labelled with coloured polymer particles (so-called lattices) or the like.

One advantageous further development of the invention may provide that one of more reagents which can be detached by the sample are provided in the three-dimensional structure, and one reagent is applied to the stirring device in such a way that it is substantially non-detachable from the stirring device during stirring of the sample of fluid.

If may conveniently be provided that the detachable reagent(s) are analyte-specific binding partners, in particular antibodies, which are optionally labelled, and the at least one reagent which reacts with the analyte is configured so as to immobilise the analyte or a complex formed of the analyte and one or more of the detachable reagents.

Advantageous embodiments of the method for determining an analyte in a fluid will be explained in more detail below.

One advantageous embodiment of the invention provides that the at least one reagent which reacts with the analyte is at least partially detached from the stirring device during stirring of the sample of fluid, and detached reagent is at least partially dissolved in the sample of fluid.

One further development of the invention provides that the at least one reagent which reacts with the analyte is at least partially detached in some layers or surface regions from the stirring device during stirring of the sample of fluid.

In one advantageous embodiment of the invention, it may be provided that the at least one reagent which reacts with the analyte remains at least partially non-detached on the stirring device during stirring of the sample of fluid.

One embodiment may provide that the at least one reagent reacts with the analyte in a reaction zone of the three-dimensional structure. One further development provides that the at least one reaction product or optionally the further reaction product formed by the reaction product is detected in a detection zone of the three-dimensional structure. The sample of fluid can be transported in an optionally microfluidic channel structure of the three-dimensional structure using capillary forces. It may also be provided to move the sample by means of pumps or suction means or by using centrifugal forces.

In one convenient embodiment of the invention, it may be provided that one or more complexes selected from the following group of complexes are immobilised in the three-dimensional structure on an immobilised trapping reagent in a trapping zone: the analyte, the reaction product and the further reaction product.

One further development of the invention provides that the analyte reacts with at least one further reagent, with which a wall of the three-dimensional structure is loaded at least in wall sub-regions.

In one advantageous embodiment of the invention, it may be provided that the at least one reagent which reacts with the analyte and optionally the at least one further reagent which reacts with the analyte contain one or more reagent constituents selected from the following group of reagent constituents: luminescent dye, phosphorescent dye, absorption dye, coloured particles, labelled antibodies, and antibodies with a binding group for binding the antibodies to an associated receptor.

One further development of the invention may provide that stirring movements of the stirring device are driven by means of at least one magnetic field.

The additionally proposed stirring device which can be operated in a contactless manner may in advantageous embodiments be designed as described above in respect of the stirring device in connection with the apparatus for determining an analyte.

Figure 2:
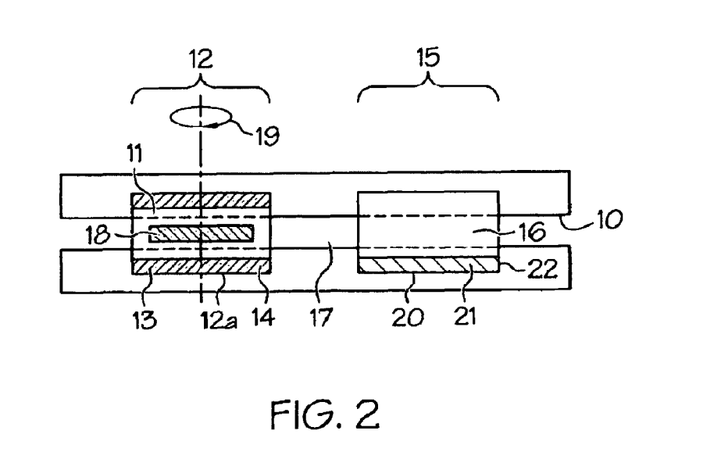
FIG. 2 shows a schematic view of an apparatus for determining an analyte in a fluid, the apparatus comprising a three-dimensional structure in which a reagent zone and a reaction zone are formed together in one section and a detection zone is also formed.

FIG. 2 shows a schematic view of an apparatus for determining an analyte, the apparatus comprising a three-dimensional structure 10. The three-dimensional structure 10 is formed with a reagent zone 13 and a reaction zone 14 in one section 12 and with a detection zone 16 in a further section 15 downstream of the section 12. In the three-dimensional structure 10, the section 12 and the further section 15 are connected via a channel 17, so that a fluid can pass from the section 12 into the further section 15.

In different embodiments, by choosing the spatial dimensions, the three-dimensional structure 10 is optionally designed as a microfluidic structure or as a non-microfluidic structure (macroscopic structure). By way of example, the three-dimensional structure 10 can be produced by means of microtitre plates. The three-dimensional structure 10 can also be formed in an injection-moulded component. Another possibility for producing the three-dimensional structure 10 consists in laser machining a suitable material, for example a plastic, a semiconductor material or a metal.

Another possibility for producing the three-dimensional structure 10 consists in using an assembly of layer-type materials. By way of example, a double-sided adhesive tape provided with cutouts can be applied to a flat plastic film and, after introducing the appropriate reagents, closed with a further flat plastic film. In this case, the double-sided adhesive tape serves as a spacer for the two flat films and at the same time, via the cutouts, defines opening structures, chamber structures and channel structures.

The dimensions of the three-dimensional structure 10 can in this case be selected such that a fluid is transported in the three-dimensional structure 10 means of capillary forces at least in sub-sections. By suitably selecting the dimensions and shape of the three-dimensional structure 10, the flow conditions in the three-dimensional structure 10 can be adapted to the intended use, for example in order to take account of different viscosities of fluids which contain the analyte to be determined.

In order to determine the analyte, a sample of the fluid containing the analyte, for example a body fluid such as urine or blood, is introduced into the three-dimensional structure 10. The sample of fluid then passes firstly into the section 12, in which there are formed the reagent zone 13, namely a section of the three-dimensional structure 10 in which one or more reagents which react with the analyte are arranged, and the reaction zone 14. A magnetic stirring device in the form of a stirring element 18 is arranged in the section 12. The stirring element 18 can be set in rotational movements by using an external magnetic field 19, so that a stirring zone 11 in which the sample of fluid is stirred is formed in the section 12.

The stirring element 18 is loaded with a reagent which, as the stirring element 18 rotates in the sample of fluid, gradually detaches from the stirring element 18 and is mixed with the sample of fluid. Further reagents are formed on a wall 12a in the section 12. In the reaction tone 14, which at least partially overlaps with the reagent zone 13 and the stirring zone 11, the reagents then react with the analyte in the fluid, as a result of which a reaction product is formed. The stirring operation by means of the stirring element 18 helps the reagents both to detach from the stirring element 18 and the wall 12a and to mix with the sample of fluid. Both processes are accelerated by the rotation of the stirring element 18.

Once the reaction between the detached reagents and the analyte of the fluid has taken place in the reaction zone 14 formed in the section 12, the sample of fluid is moved through the channel 17 into the detection zone 16 in the further section 15 of the three-dimensional structure 10. This optionally takes place by means of capillary forces. The sample of fluid may also be pumped out of the section 12, through the channel 17 and into the further section 15, for example by means of a micropump (not shown). It is also possible to transfer the sample of fluid from the section 12 into the further section 15 by means of gravitational forces or centrifugal forces. Of course, the different ways of transferring the sample of fluid from the reaction zone 14 to the detection zone 16 can also be combined with one another.

In the detection zone 16, the reaction product is then detected by means of a detection method, which may be for example an optical or some other physical method, an electrochemical or some other chemical method.

In the schematic diagram as shown in FIG. 2, a further reagent 21 is immobilised in the region of a wall 20 of the detection zone 16. The further reagent 21 serves as a trapping reagent by binding the reaction product, which was formed in the reaction zone 14 during the reaction between the analyte in the sample of fluid and the reagent on the stirring element 18, to the further reagent, which in one embodiment is streptavidin for example. By means of the further reagent 21, a trapping zone 22 is formed as a further functional zone in the three-dimensional structure 10. After the binding to the further reagent 21 which acts as a trapping reagent, the detection of the analyte can be carried out in the detection zone 14. One advantage associated with the binding of the reaction product in the trapping zone 22 is that the reaction product can be washed with further aliquots of the sample of fluid or with a different fluid. Another advantage is that easy optical conditions for optical analysis exist in the region of the quasi-planar trapping zone 22.

In the method for determining the analyte, the step of determining the analyte may be carried out once parasitic substances have been removed from the three-dimensional structure 10 by washing. For the washing operation, use may be made for example of an excess of sample or else of a separately supplied washing fluid, for example a washing buffer.

Figure 3A:
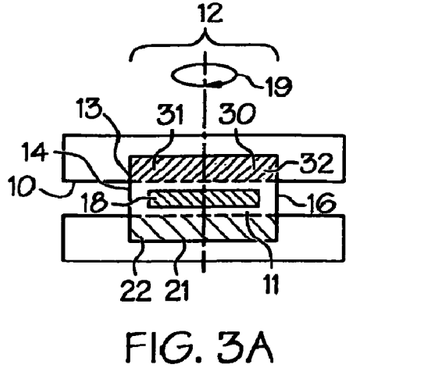
FIG. 3a shows a schematic view of an apparatus for determining an analyte in a fluid, the apparatus comprising a three-dimensional structure in which a reagent zone, a reaction zone and a detection zone are formed together in one section.

FIG. 3a shows a schematic view of an apparatus for determining an analyte in a fluid, the apparatus comprising a three-dimensional structure in which, unlike in the embodiment shown in FIG. 2, a reagent zone, a reaction zone and a detection zone are formed together in one section of the three-dimensional structure. For identical features, the same references as in FIG. 2 are used in FIG. 3.

Unlike the apparatus shown in FIG. 2, the apparatus for determining the analyte shown schematically in FIG. 3a is formed in such a way that the reagent zone 13, the reaction zone 14 and the detection zone 16 are all formed in the section 12. The stirring element 18 is once again loaded with at least one reagent which reacts with the analyte in the sample of fluid. In the region of section 12 of the three-dimensional structure 10, a layer arrangement 30 comprising a first and a second reagent 31, 32 which react with the analyte in the fluid is formed on the wall. As a result of the stirring with the stirring element 18, the first and the second reagent 31, 32 of the layer arrangement 30 are detached from the wall, mixed with the sample of fluid and dissolved in the sample of fluid. In one embodiment, the first reagent 31 and the second reagent 32 react to form a reaction product, for example a sandwich-type compound, which is then bound to a further reagent 21 which acts as a trapping reagent in the trapping zone 22. In order to remove any unbound reagents, section 12 of the three-dimensional structure 10 can be rinsed with a different fluid or with an aliquot of the sample before the actual determination of the analyte.

Figure 3B:
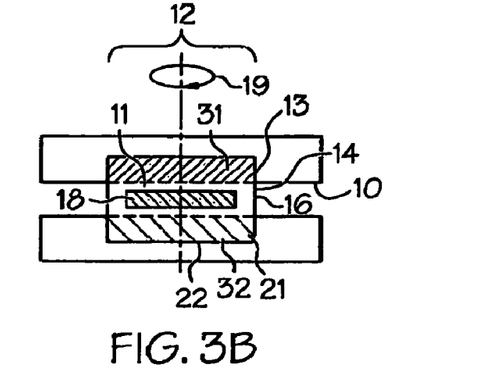
FIG. 3b shows a schematic view of an apparatus for determining an analyte in a fluid, the apparatus comprising a three-dimensional structure according to FIG. 3a in another embodiment.

FIG. 3b shows a schematic view of an apparatus for determining an analyte in a fluid, the apparatus comprising a three-dimensional structure according to FIG. 3a in another embodiment. The second reagent 32, which in the embodiment shown in FIG. 3a forms part of the layer arrangement 30, is now immobilised together with the trapping reagent 21 in the trapping zone 22, so that a complex composed of the analyte and the first reagent 31 accumulates in the trapping zone 22 during the determination of the analyte. The second reagent 32 and the trapping reagent 21 can be accommodated in spatially separate zones in the trapping zone, for example in a striped or dotted pattern.

Figure 4:
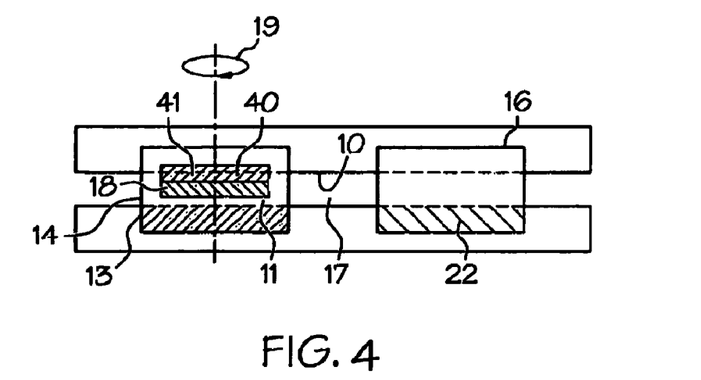
FIG. 4 shows a schematic view of an apparatus for determining an analyte in a fluid, the apparatus comprising a three-dimensional structure according to FIG. 2, wherein a reagent which reacts with the analyte is formed in a layer on a stirring element.

FIG. 4 shows a schematic view of an apparatus for determining an analyte in a fluid, the apparatus comprising a three-dimensional structure according to FIG. 2. For identical, features, the same references as in the previous FIGS. 2, 3a and 3b are used in FIG. 4. The stirring element 18 is loaded with a reagent 40 in the form of a dry reagent, which is applied as a layer 41.

Figure 5:
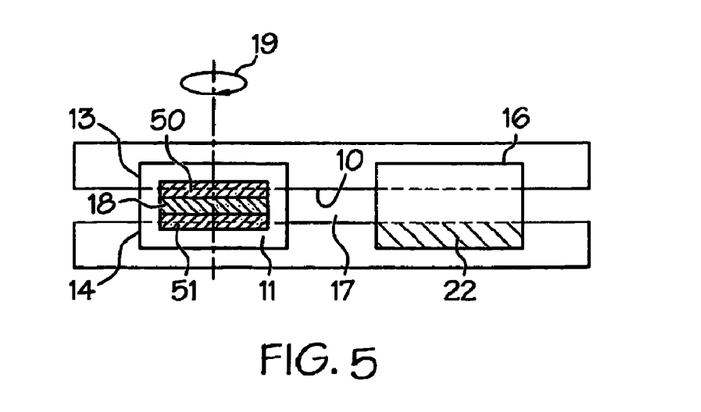
FIG. 5 shows a schematic view of an apparatus for determining an analyte in a fluid, the apparatus comprising a three-dimensional structure according to FIG. 2, wherein a plurality of reagents which react with the analyte are formed exclusively on the stirring element.

FIG. 5 shows a schematic view of an apparatus for determining an analyte in a fluid, the apparatus comprising a three-dimensional structure according to FIG. 2. For identical features, the same references as in the previous FIGS. 2 to 4 are used. A plurality of reagents 50, 51 which react with the analyte are formed exclusively on the stirring element 18. The plurality of reagents 50, 51 are arranged on an upper side and an underside of the stirring element 18.

Figure 6:
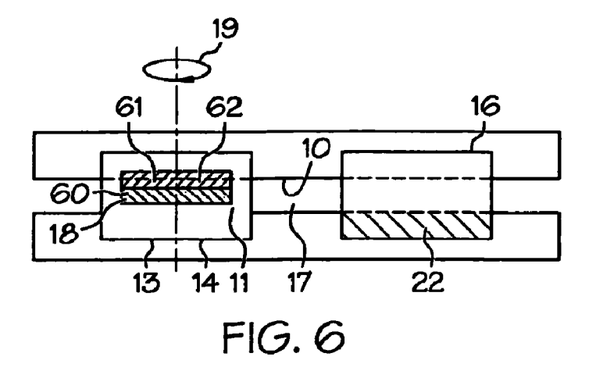
FIG. 6 shows a schematic view of an apparatus for determining an analyte in a fluid, the apparatus comprising a three-dimensional structure according to FIG. 2, wherein sub-regions of a surface of the stirring element are loaded with different reagents which react with the analyte.

FIG. 6 shows a schematic view of an apparatus for determining an analyte in a fluid, the apparatus comprising a three-dimensional structure according to FIG. 2. For identical features, the same references as in the previous FIGS. 2 to 5 are used. The stirring element is loaded with different reagents 61, 62 in sub-regions of a surface 60 of the stirring element 18. All the outer surfaces of the stirring element 18 can be used for this.

Figure 7:
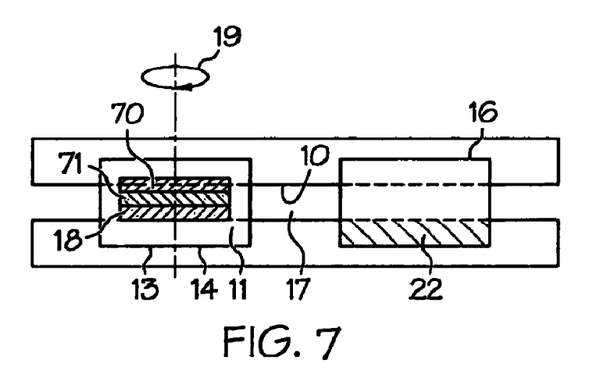
FIG. 7 shows a schematic view of an apparatus for determining an analyte in a fluid, the apparatus comprising a three-dimensional structure according to FIG. 2, wherein a plurality of reagents are formed in a layer arrangement one on top of the other on the stirring element.

FIG. 7 shows a schematic view of an apparatus for determining an analyte in a fluid, the apparatus comprising a three-dimensional structure according to FIG. 2. For identical features, the same references as in the previous FIGS. 2 to 6 are used. A plurality of reagents 70 are formed one on top of the other in a layer arrangement 71 on the stirring element 18.

Figure 8:
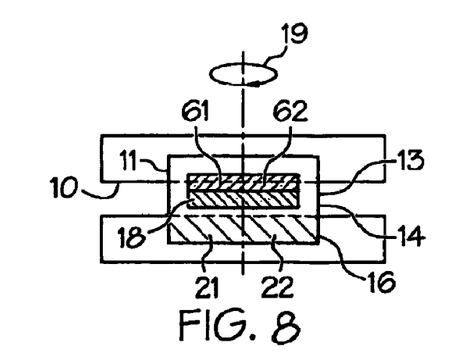
FIG. 8 shows a schematic view of an apparatus for determining an analyte in a fluid, the apparatus comprising a three-dimensional structure according to FIG. 3a, wherein a plurality of reagents which react with the analyte are formed in different sub-regions of the surface of the stirring element.

FIG. 8 shows a schematic view of an apparatus for determining an analyte in a fluid, the apparatus comprising a three-dimensional structure according to FIG. 3a. For identical features, the same references as in the previous FIGS. 2 to 7 are used.

A plurality of reagents 61, 62 which react with the analyte are formed in different sub-areas of the stirring element 18. Typically, the reagents 61, 62 which react with the analyte can be detached from the stirring element 18 in the presence of the sample fluid. As an alternative, it is possible to provide the reagents 61, 62 instead of the trapping reagent 21 on one or more walls of the apparatus in a form that can be detached by the sample fluid, and to immobilise the trapping reagent 21 on the stirring element 18. By way of example, the reagent 61 may be a biotinylated anti-analyte antibody and the reagent 62 may be an anti-analyte antibody conjugated with an optically or visually detectable label. The trapping reagent 21 may be (poly)streptavidin. In the presence of the analyte in the fluid sample, the detection reaction for the analyte is started by the dissolving of the reagents 61, 62. In the sample fluid, so-called sandwich complexes composed of biotinylated anti-analyte antibody, analyte and labelled anti-analyte antibody conjugate are formed. By moving the stirring element 18, which is symbolised by the schematically shown rotational movement 19 in FIGS. 2 to 10, it becomes easier to dissolve the reagents 61, 62 and to mix them through the sample. The trapping of the sandwich complexes composed of the analyte and associated binding partners by the trapping zone 22 is also facilitated, the trapping zone in this case being located on the stirring element 18. For the detection, the stirring element 18 is typically stopped, and can be held by magnetic fields at one side of the apparatus comprising the three-dimensional structure 10, so that reproducible optical conditions are achieved particularly for optical detection methods.

Figure 9:
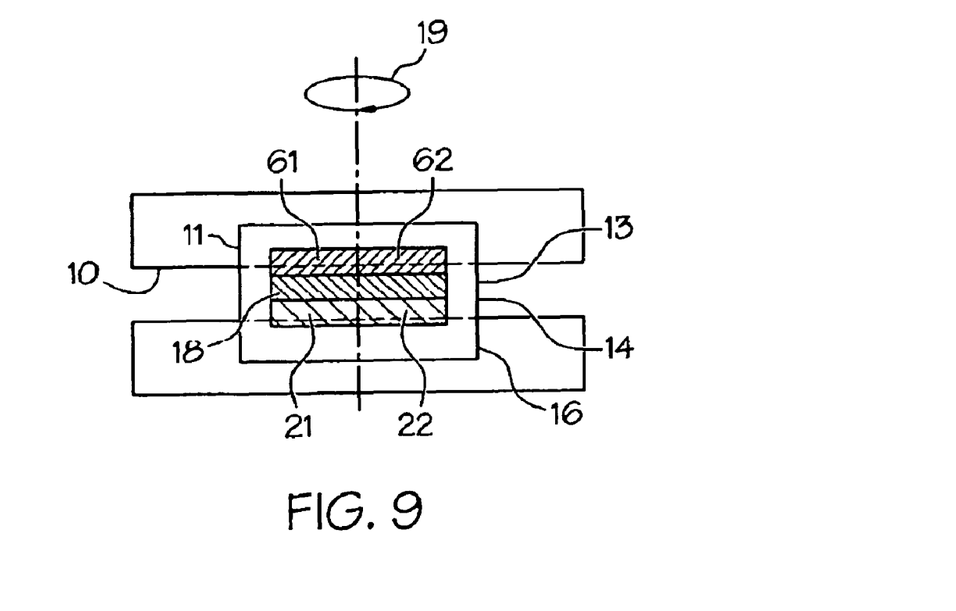
FIG. 9 shows a schematic view of an apparatus for determining an analyte in a fluid, the apparatus comprising a three-dimensional structure according to FIG. 5a, wherein a trapping reagent is formed on the stirring element.

FIG. 9 shows a schematic view of an apparatus for determining an analyte in a fluid, the apparatus comprising a three-dimensional structure according to FIG. 3a. For identical features, the same references as in the previous FIGS. 2 to 8 are used. A trapping reagent 21 is formed on the stirring element 18. On the other side, the stirring element 18 is loaded in sub-areas with further reagents 61, 62 which are applied to the stirring element 18.

Figure 10:
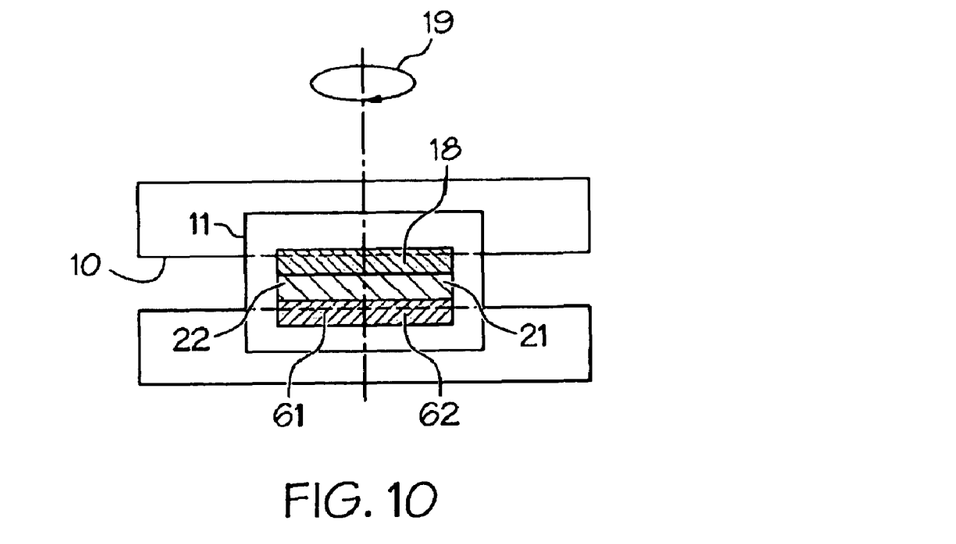
FIG. 10 shows a schematic view of an apparatus for determining an analyte in a fluid, the apparatus comprising a three-dimensional structure according to FIG. 3, wherein a trapping reagent on the stirring element is superposed with reagents which react with the analyte.

FIG. 10 shows a schematic view of an apparatus for determining an analyte in a fluid, the apparatus comprising a three-dimensional structure according to FIG. 3a. For identical features, the same references as in the previous FIGS. 2 to 9 are used. Unlike the embodiment shown in FIG. 9, the trapping reagent 21 on the stirring element 18 is superposed with the further reagents 61, 62 in sub-areas. During stirring of the sample of fluid with the stirring element 13, firstly the further reagents 60, 61 detach and react with the analyte. Thereafter, the reaction product thus formed accumulates in the trapping zone 22 at the trapping reagent 21, which in turn is formed on the stirring element 18 in such a way that it does not detach into the fluid as a result of the stirring.

In the preceding examples of embodiments, the three-dimensional structure 10 has been described with the section 12 and optionally with the further section 15. In other embodiments, additional sections may be provided in order to form the different zones individually for each section of the three-dimensional structure 10 or in any combinations. The described possibilities for arranging and immobilising the reagents in the different areas of the three-dimensional structure 10 and on the stirring element 18 can also be combined with one another at will. The stirring zone 11 is then formed in the region of the three-dimensional structure 10 in which the stirring element 18 is arranged. Including the regions of the three-dimensional structure 10 in which reagents which react with the analyte to be determined are deposited before accumulation to the optionally provided trapping zone, generally a zone is formed which is also referred to as the reagent zone. This zone may spatially overlap with other zones in the three-dimensional structure 10, for example the reaction zone and the detection zone. In addition, a section may be provided in which a waste zone is formed. The waste zone is usually provided at the end in the chain of zones.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative of additional features that may or may hot be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An apparatus for determining an analyte in a fluid, comprising a stirring zone formed in a three-dimensional structure, into which stirring zone a sample of the fluid can be introduced and in which there is a stirring device which can be operated in a contactless manner, said stirring device being configured so as to stir the sample of fluid introduced into the stirring zone and being loaded with at least one reagent which reacts with the analyte, wherein the stirring device is a magnetic stirring device comprising one or more magnetic strip sections which form stirring elements, and wherein the at least one reagent is partially detachable from the stirring device during stirring the sample.

2. The apparatus according to claim 1, wherein the stirring one is formed in a microfluidic three-dimensional structure.

3. The apparatus according to claim 1, wherein the stirring device is designed as a microstirrer.

4. The apparatus according to claim 1, wherein the stirring device has pore structures with pores in which the at least one reagent which reacts with the analyte is at least partially embedded.

5. The apparatus according to claim 1, wherein the stirring device comprises a film with a magnetic layer.

6. The apparatus according to claim 1, wherein the stirring device has at least one stirring sub-element selected from the group consisting of a laminated section, a woven section, a nonwoven section, a membrane section, and a film section.

7. The apparatus according to claim 1, wherein the stirring device is loaded with a second reagent which reacts with the analyte, and wherein the second reagent which reacts with the analyte is bound to the stirring device by at least one binding type selected from the group consisting of partially detachable from the stirring device during stirring of the sample of fluid, substantially completely detachable from the stirring device during stirring of the sample of fluid, and substantially non-detachable from the stirring device during stirring of the sample of fluid.

8. The apparatus according to claim 1, wherein the stirring device has, at least in sub-regions, a coating which optionally promotes the adhesion of the at least one reagent which reacts with the analyte.

9. The apparatus according to claim 1, wherein the at least one reagent which reacts with the analyte is formed as at least one dry reagent on the stirring device.

10. The apparatus according to claim 1, wherein the at least one reagent which reacts with the analyte is formed in a layer arrangement on the stirring device, which layer arrangement at least partially covers one surface of the stirring device.

11. The apparatus according to claim 10, wherein the layer arrangement comprises superposed layers of different reagents which react with the analyte.

12. The apparatus according to claim 11, wherein the different reagents in the layers or in layer arrangement which react with the analyte have different solubilities during stirring of the sample of fluid with the stirring device.

13. The apparatus according to claim 1, wherein a trapping zone is also formed in the three-dimensional structure, a trapping reagent being immobilised in said trapping zone.

14. The apparatus according to claim 1, wherein one or more zones are arranged downstream of the stirring zone in the three-dimensional structure and are connected to the stirring zone via an optionally microfluidic channel structure, said one or more zones selected from the group consisting of a reaction zone, a detection zone, a trapping zone, and a waste zone, selected from the group consisting of a reaction zone, a detection zone, a trapping zone, and a waste zone.

15. The apparatus according to claim 1, wherein one or more zones are formed in the three-dimensional structure and are integrated with the stirring zone, said one or more zones selected from the group consisting of a reaction zone, a detection zone, a trapping zone, and a waste zone.

16. The apparatus according to claim 1, wherein a wall of the three-dimensional structure is loaded at least in wall sub-regions with at least one further reagent which reacts with the analyte.

17. The apparatus according to claim 1, wherein the at least one reagent which reacts with the analyte and optionally an at least one further reagent which reacts with the analyte contain one or more reagent constituents selected from the group consisting of luminescent dye, phosphorescent dye, absorption dye, coloured particles, labelled antibodies, and antibodies with a binding group for binding the antibodies to an associated receptor.

18. The apparatus according to claim 1, wherein one of the at least one reagents is applied to the stirring device in such a way that it non-detachable from the stirring device during stirring of the sample of fluid.

19. The apparatus according to claim 18, wherein the detachable reagent(s) are analyte-specific binding partners, which are optionally labelled, and the at least one reagent which reacts with the analyte is configured so as to immobilise the analyte or a complex formed of the analyte and one or more of the detachable reagents.

20. The apparatus according to claim 19, wherein the analyte-specific binding partners are antibodies.

21. A stirring device which can be operated in a contactless manner, being loaded with at least one reagent which reacts with an analyte, wherein said stirring device is designed as a magnetic stirring device comprising one or more magnetic strip sections which form stirring elements, and wherein the at least one reagent is partially detachable from the stirring device during stirring of a sample of fluid.

22. The stirring device according to claim 21, further comprising pore structures with pores in which the at least one reagent which reacts with the analyte is at least partially embedded.

23. The stirring device according to claim 21 further comprising a film with a magnetic layer.

24. The stirring device according to claim 21 further comprising at least one stirring sub-element selected from the group consisting of a laminated section, a woven section, a nonwoven section, a membrane section, and a film section.

25. The stirring device according to claim 21, wherein the stirring device is loaded with a second reagent which reacts with the analyte, and wherein the second reagent which reacts with the analyte is bound by at least one binding type selected from the group consisting of partially detachable during stirring of the sample of fluid, substantially detachable during stirring of the sample of fluid, and substantially non-detachable during stirring of the sample of fluid.

26. The stirring device according to claim 21 further comprising a coating formed at least in sub-regions, which coating optionally promotes the adhesion of the at least one reagent which reacts with the analyte.

27. The stirring device according to claim 21, wherein the at least one reagent which reacts with the analyte is formed as at least one dry reagent.

28. The stirring device according to claim 21, wherein the at least one reagent which reacts with the analyte is formed in a layer arrangement which at least partially covers one surface.

29. The stirring device according to claim 28, wherein the layer arrangement comprises superposed layers of different reagents which react with the analyte.

30. The stirring device according to claim 29 wherein the different reagents in the layers or in the layer arrangement which react with the analyte have different solubilities during stirring of the sample of fluid with the stirring device.

* * * * *